US007673406B2

(12) United States Patent
Giro Amigo

(10) Patent No.: US 7,673,406 B2
(45) Date of Patent: Mar. 9, 2010

(54) HANGING LAMINAR LABEL AND ROLL OF LABELS

(75) Inventor: Ezequiel Giro Amigo, Badalona (ES)

(73) Assignee: Giro GH, S.A., Badalona (ES)

( * ) Notice: Subject to any disclaimer, the term of this patent is extended or adjusted under 35 U.S.C. 154(b) by 0 days.

(21) Appl. No.: 12/132,931

(22) Filed: Jun. 4, 2008

(65) Prior Publication Data

US 2008/0301981 A1 Dec. 11, 2008

(30) Foreign Application Priority Data

Jun. 8, 2007 (ES) ................................ 200701584

(51) Int. Cl.

| | |
|---|---|
| ***G09F 3/10*** | (2006.01) |
| ***A44C 5/00*** | (2006.01) |
| ***A61B 5/103*** | (2006.01) |
| ***A61B 5/117*** | (2006.01) |
| ***B65D 65/28*** | (2006.01) |
| ***B42D 19/00*** | (2006.01) |
| ***G09C 3/00*** | (2006.01) |

(52) U.S. Cl. ........................ 40/299.01; 40/633; 40/674; 40/672; 40/638; 428/43; 281/5; 283/75; 283/81

(58) Field of Classification Search .............. 40/299.01, 40/633, 674, 672, 638; 428/43; 281/5; 283/75, 283/81

See application file for complete search history.

(56) References Cited

U.S. PATENT DOCUMENTS

| | | | | |
|---|---|---|---|---|
| 3,764,447 A * | 10/1973 | Duff | ............................ | 428/43 |
| 4,226,036 A * | 10/1980 | Krug | ........................... | 40/633 |
| 7,197,842 B2 * | 4/2007 | Ali | .............................. | 40/633 |
| 7,246,459 B2 * | 7/2007 | Lewis | .......................... | 40/673 |

FOREIGN PATENT DOCUMENTS

| | | |
|---|---|---|
| ES | 2 254 039 | 6/2006 |

* cited by examiner

*Primary Examiner*—Lesley Morris
*Assistant Examiner*—Syed A Islam
(74) *Attorney, Agent, or Firm*—Sughrue Mion, PLLC

(57) ABSTRACT

Hanging laminar label having a main portion of essentially rectangular sheet of a width H and with a longitudinal central appendage, which is essentially rectangular and of a narrower width h, wherein the appendage is attached to the main portion by a connection neck that has a central portion of a constant width z and the distal end of the appendage has a wider section with a portion of a constant width Z, the sum of the widths of the main portion and the appendage H+h being equal to the sum of the widths of the connection neck and the wider section of the appendage z+Z.

14 Claims, 2 Drawing Sheets

HANGING LAMINAR LABEL AND ROLL OF LABELS

TECHNICAL FIELD OF THE INVENTION

The invention relates to a hanging laminar label, consisting of a main portion that is essentially rectangular with a longitudinal central appendage that is narrower than the main portion, and to a roll of labels according to the invention.

BACKGROUND OF THE INVENTION

In a known manner some mesh bags, of the type used to package fruit and vegetable products, include a hanging laminar label consisting of a main portion, generally of an essentially rectangular shape that acts as a support for printed information relating to the product packaged in the bag, which has a longitudinal appendage, the purpose of which is to connect the bag to said main portion of the label.

Normally, the appendage of the label is narrower than the rectangular portion and it is long enough for its end to be deformed when it is attached to the bag, e.g. by stapling or by heat-sealing, without this deformation affecting the essentially rectangular portion of the label and making it difficult to read the information printed thereon. Reducing the width of the appendage also makes it possible to save material when manufacturing large batches of this type of labels.

For example, patent document ES 2254039 discloses a bag for fruit and vegetable products, which consists of a woven mesh wherein a mouth for the closure of one end of the bag is in close contact with and surrounded by an appendage of a hanging label, the mouth and appendage assembly being heat-sealed using the material that constitutes the bag and the label.

However, it is disadvantageous for an appendage to be too narrow when the end of the appendage and one end of the bag, which is already gathered, are heat sealed together.

When the heat-sealing operation is carried out by ultrasound, an embodiment wherein the distal end of the appendage surrounds the end of the bag, which is already gathered, is of particular interest. For this reason the appendage is folded along a longitudinal fold line, or is simply bent, the end of the bag being trapped between the walls of the appendage. What happens is that the width of the appendage, which is reduced to save material and to prevent the rectangular portion of the label from becoming deformed, mean that it cannot completely, or almost completely, surround the thickness of material that forms the gathered end of the bag, resulting in a low aesthetic and functional quality of the heat-sealed joints.

EXPLANATION OF THE INVENTION

A first aspect of the invention discloses a hanging laminar label consisting of a main portion of sheet that is essentially rectangular with a width H, and with a longitudinal central appendage that is essentially rectangular and narrower h.

Essentially, the label is characterised in that the appendage is joined to said main portion by a connection neck with a central portion of a constant width z, and in that the distal end of the appendage has a wider section with a portion of a constant Width Z, the sum of the widths of the main portion and the appendage H+h being the equal to the sum of the widths of the connection neck and the wider section of the appendage z+Z.

According to another characteristic of the label, its vertices are rounded, and according to a particularly interesting variant, the connecting sections between the straight longitudinal portions of the main portion, the central portion of the connection neck, the appendage and the portion of a constant width of the wider section of the appendage are advantageously on a slanting plane.

According to another characteristic of the invention, the width z of the central portion of a constant width of the connection neck is narrower than the width Z of the portion of a constant width of the wider section of the appendage.

Another aspect of the invention discloses a roll of labels consisting of a continuous rollable strip of labels according to the invention, wherein said labels are longitudinally aligned and continuously joined, and are designed to be separated by transversally cutting the strip.

As will be described below in detail, the production of labels according to the invention is optimised by providing a roll consisting of a rollable sheet from which individual strips of labels according to the invention are produced using a punch roller and can be stored and supplied either rolled around themselves or rolled around a roller core.

BRIEF DESCRIPTION OF THE DRAWINGS

The attached drawings show a non-limiting example of an embodiment of the label that is the object of the invention, and a rollable sheet for manufacturing labels according to the invention and a strip of labels produced from said sheet.

Specifically.

DETAILED DESCRIPTION OF THE DRAWINGS

Figure 1:
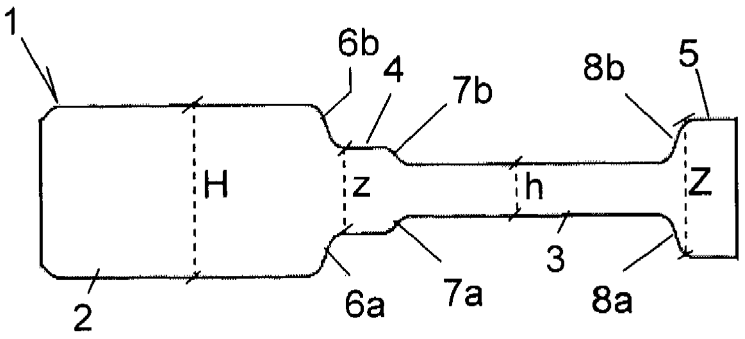
FIG. 1 is a plan view of a label according to the invention.

FIG. 1 shows a label 1 that is designed to be used as a hanging label for labelling bags, and more specifically for labelling bags of a heat-sealable material.

The label 1 is laminar and is made from a heat-sealable material. Said label 1 consists of a rectangular main portion 2 of a width H, and with a longitudinal central appendage 3 of a narrower width h.

Each of the sides of the main portion of the label 1 can be used as a support for information about the product packaged in the bag, which can be printed directly on the main portion or it can act as a base sheet for a self-adhesive label that is already printed with the desired information.

The appendage 3 acts as the connection between the main portion 2 and the bag itself, the wider section 5 of the distal end of the appendage being designed to be attached by heat-sealing to the material from which the bag is made, preferably by applying ultrasound.

Figure 4:
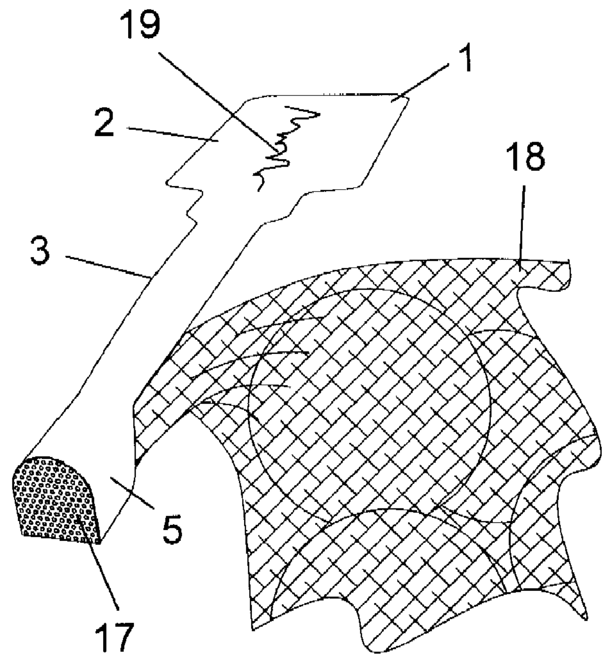
FIG. 4 shows a mesh bag that includes a label according to the invention.

FIG. 4 shows an example of application of a label 1 according to the invention, the main portion 2 of which carries the printed information 19 about the product stored in a bag 18. In the example shown here, the label 1 is attached to one end 17 of a mesh bag 18, gathered with or without a particular order. It can be observed that the wider section 5 of the appendage 3 makes it possible for this part of the label 1 to fully or partially surround said end 17 of the bag 18, which is trapped inside the wider section 5 that surrounds it.

The label 1 of FIG. 1 can be produced from a continuous sheet of heat-sealable material, from which longitudinal strips can be cut, punched or, in short, separated by any means, from which the labels can be separated by transversally cutting. Naturally, the sheet must be cut according to the contour of the individual labels that are to be produced.

In terms of this contour, it should be mentioned that the vertices of the label 1 shown here are rounded, and that the connecting sections 6*a*, 6*b*; 7*a*, 7*b*; and 8*a*, 8*b* between the straight longitudinal portions of the main portion 2 of the of the central portion of the connection neck 4, the appendage 3 and the portion of a constant width of the wider section 5 of the appendage are advantageously on a slanting plane.

Figure 2:
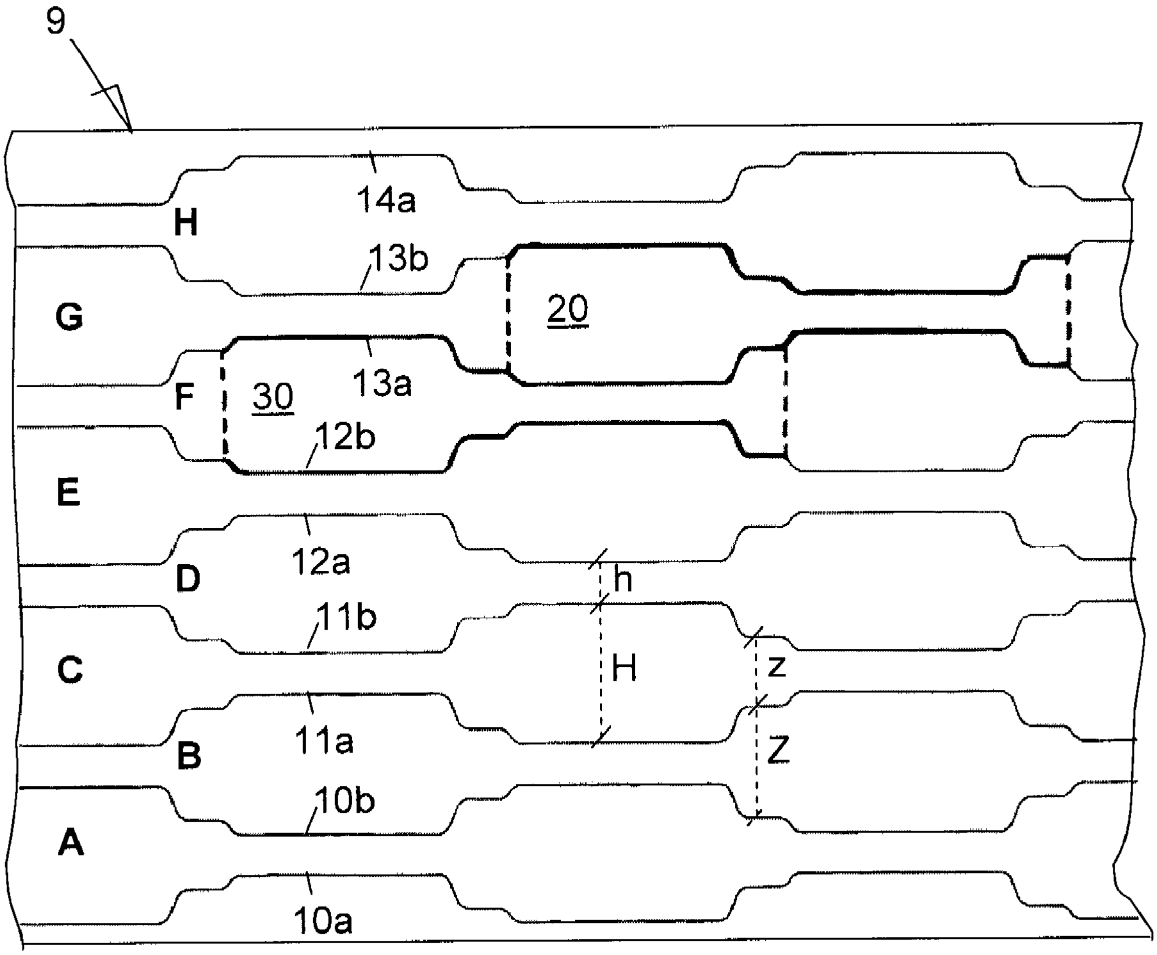
FIG. 2 is a plan view of a longitudinal portion of rollable sheet on which a number of separation lines are indicated, determining pairs of strips of labels as shown in FIG. 1.

FIG. 2 shows a portion of a rollable sheet 9 on which a number of imaginary longitudinal separation lines 10*a*, 10*b*, 11*a*, 11*b*, 12*a*, 12*b*, 13*a*, 13*b* and 14*a* are indicated, determining pairs of strips A, C, E, and G of labels, the labels of each strip being longitudinally and continuously joined, and designed to be separated by transversal cutting their respective strip.

In order to make maximum use of the material of the sheet 9, and to thus reduce the amount of material that cannot be used to produce strips of labels, the label 1 advantageously has a connection neck 4 between the main portion 2 and the appendage 3 that complements the wider section 5 of the distal end of said appendage 3, with a portion of a constant width Z, when the sheet 9 on either side of any strip of labels separated from said sheet 9 is to be used.

For this purpose, firstly, the connection neck 4 has a central portion of a constant width z, the sum z+Z of the widths of this central portion of a constant width z of the connection neck 4 and the portion of a constant width Z of the wider section 5 of the appendage 3 being equal to the sum H+h of the widths H and h of the main portion 2 and the appendage 3, respectively, and secondly, the means of cutting, e.g. a punch roller, is adapted so that it cuts along said separation lines 10*a*, 10*b*, 11*a*, 11*b*, 12*a*, 12*b*, 13*a*, 13*b*, which are symmetrically positioned in pairs, each pair of separation lines also being symmetrically positioned in relation to another adjacent pair of separation lines, so that respective strips of labels are also determined between each pair of separation lines, being longitudinally off-centre in relation to the labels of their adjoining strips.

Effectively, in FIG. 2 it can be seen that the pairs of longitudinal separation lines 10*a*, 10*b*, 11*a*, 11*b*, 12*a*, 12*b*, 13*a*, 13*b* determine strips A, C, E and G of labels, the labels of each strip being longitudinally and continuously joined, and designed to be separated by transversally cutting the strip.

For example, in strips F and G thicker lines have been used to indicate the contour of respective labels 20 and 30, which would be produced by separating said strips F and G from the sheet 9 and then transversally cutting them along the broken lines.

It can also be observed that each pair 10*a* and 10*b*; 11*a* and 11*b*; 12*a* and 12*b*; and 13*a* and 13*b* of separation lines can be positioned symmetrically in relation to the adjacent pair of separation lines, so that respective essentially rectangular main portions of a width H, connection necks with a portion of a constant width z, appendages of a width h, and wider sections of the appendages with a portion of a constant width Z of successive labels of respective strips of labels are also determined between each pair of separation lines. Thus, it can be seen that strips B, D, F and H are determined between the longitudinal separation lines 10*b* and 11*a*; 11*b* and 12*a*; 12*b* and 13*a*; and 13*b* and 14*a*, being longitudinally off-centre in relation to the adjoining strips A, C, E and G.

Figure 3:
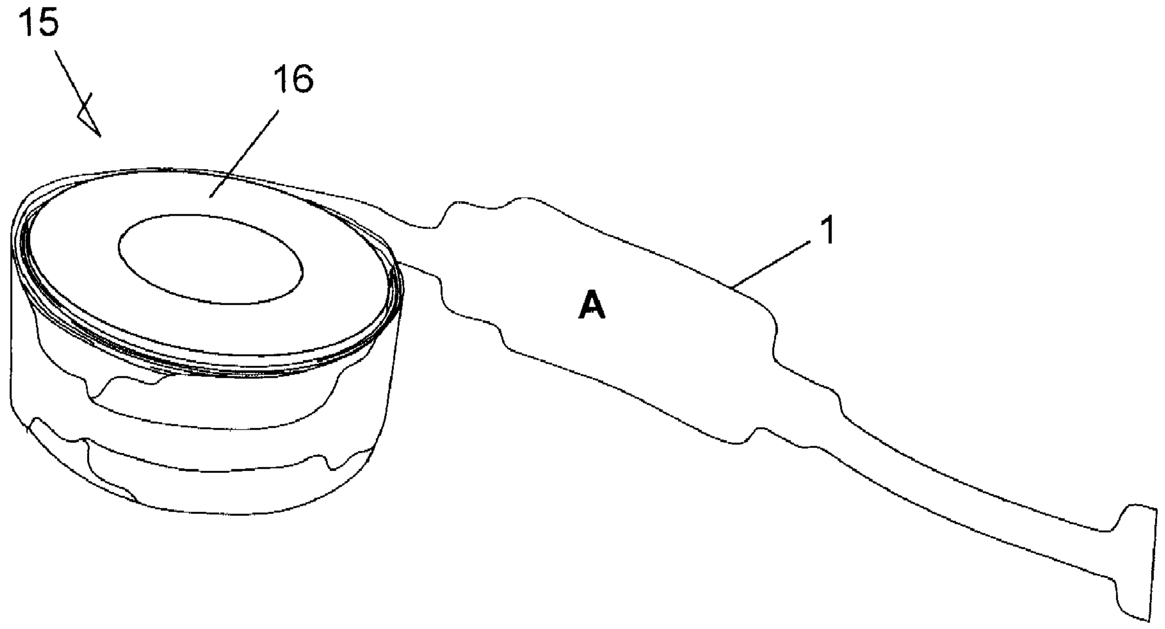
FIG. 3 shows a roll of labels in which a strip of labels, which is produced by cutting the sheet shown in FIG. 2 along the given cutting lines, is rolled around a hollow cylindrical core.

As has been mentioned above, the continuous sheet from which the strips of labels are produced can be cut along separation lines similar to those indicated in FIG. 2 by any known means, e.g. using a punch roller, the means of cutting of which follows the shape of the contour and the arrangement of the different separation lines. For example, from the sheet 9 shown in FIG. 2 it is possible to produce eight strips of labels A, B, C, D, E, F, G and H, respectively, which can be individually supplied, either rolled around themselves or rolled around a roller core 16, such as that shown in FIG. 3, which is normally made from cardboard or plastic, to form rolls 15.

The invention claimed is:

1. A hanging laminar label (1, 20, 30), comprising a main portion (2) of essentially rectangular sheet of a width H and with a longitudinal central appendage (3), which is essentially rectangular and of a narrower width h, wherein the appendage is attached to said main portion by a connection neck (4) that has a central portion of a constant width z, and in that the distal end of the appendage has a wider section (5) with a portion of a constant width Z, the sum of the widths of the main portion and the appendage H+h being equal to the sum of the widths of the connection neck and the wider section of the appendage z+Z.

2. The label (1, 20, 30) according to claim 1, wherein vertices of the label are rounded.

3. The label (1) according to claim 1, wherein connecting sections (6*a*, 6*b*; 7*a*, 7*b*; and 8*a*, 8*b*) between the straight longitudinal portions of the main portion (2), the central portion of the connection neck (4), the appendage (3) and the portion of a constant width of the wider section (5) of the appendage are advantageously on a slanting plane.

4. The label (1, 20, 30) according to claim 1, wherein the width z of the central portion of a constant width of the connection neck (4) is narrower than the width Z of the portion of a constant width of the wider section (5) of the appendage (3).

5. A roll of labels (15) consisting of a continuous rollable strip (A) of labels (1) according to claim 1, wherein said labels are longitudinally aligned and continuously joined, and are designed to be separated by transversally cutting the strip.

6. The hanging laminar label according to claim 1, wherein the constant width Z of the distal end is constant along a longitudinal axis of the laminar label;

wherein the longitudinal axis is an axis along which the main portion, neck portion, appendage and distal end are disposed.

7. The hanging laminar label according to claim 1, wherein the distal end of the appendage having a wider width is configured to be wrapped, about a longitudinal axis of the label, around a gathered end of a bag;

wherein the longitudinal axis is an axis along which the main portion, neck portion, appendage and distal end are disposed.

8. A label comprising in order in a longitudinal direction:

a main portion having a width H in a transverse direction;

a neck portion attached to the main portion, the neck portion having a width z in the transverse direction;

an appendage attached to the neck portion, the appendage having a width h in the transverse direction;

a distal end attached to the appendage, the distal end having a width Z in the transverse direction;

wherein H+h equals Z+z.

9. A row of labels comprising:

a plurality of labels according to claim 8;

wherein the main portion of a first label of the plurality of labels is connected to the distal end of a second label of the plurality of labels.

10. A plurality of rows of labels according to claim 9, wherein the plurality of rows are formed from a single sheet by cutting the sheet; and wherein a cut edge of a first row and a cut edge of a second row are simultaneously formed when the sheet is cut.

11. The plurality of rows of labels according to claim 10, wherein the cut edge of a main portion of a label in the first row corresponds with the cut edge of an appendage of a label in the second row; and wherein the cut edge of a distal end of a label in the first row corresponds with the cut edge of a neck portion of a label in the second row.

12. The plurality of rows of labels according to claim 10, wherein there is no lost material between the plurality of rows.

13. The label according to claim 8, wherein the distal end is configured to be wrapped, about an axis in the longitudinal direction, around a gathered end of a bag.

14. The label according to claim 8, wherein the widths H, Z, z, and h are all constant.

* * * * *